United States Patent [19]
Purdy

[11] Patent Number: 5,857,970
[45] Date of Patent: Jan. 12, 1999

[54] METHOD AND APPARATUS FOR CARDIAC-SYNCHRONIZED PERIPHERAL MAGNETIC RESONANCE ANGIOGRAPHY

[75] Inventor: David E. Purdy, East Windsor, N.J.

[73] Assignee: Siemens Medical Systems, Inc., Iselin, N.J.

[21] Appl. No.: 879,938

[22] Filed: Jun. 20, 1997

[51] Int. Cl.⁶ ................................................. A61B 5/055
[52] U.S. Cl. ........................... 600/413; 600/419; 600/509
[58] Field of Search ..................................... 600/413, 419, 600/509, 521

[56] References Cited

U.S. PATENT DOCUMENTS

| | | | |
|---|---|---|---|
| 5,320,099 | 6/1994 | Roberts et al. | 600/419 |
| 5,348,012 | 9/1994 | Kojima | 600/419 |
| 5,492,124 | 2/1996 | Purdy | 600/413 |

*Primary Examiner*—Ruth S. Smith
*Attorney, Agent, or Firm*—Mark H. Jay

[57] ABSTRACT

A subtraction MRA image is formed by subtracting a mask image formed from diastolic MR image data from an angiographic image formed from systolic MR image data. To permit acquisition of diastolic MR image data during regurgitation of arterial bloodflow, a saturation slab is established immediately adjacent the slice of interest and slightly overlapping it on its arterially downstream side.

6 Claims, 5 Drawing Sheets

METHOD AND APPARATUS FOR CARDIAC-SYNCHRONIZED PERIPHERAL MAGNETIC RESONANCE ANGIOGRAPHY

BACKGROUND OF THE INVENTION

The invention relates to magnetic resonance angiography (MRA), and more particularly relates to subtraction MRA. In its most immediate sense, the invention relates to the suppression of non-blood tissue, e.g. fat and/or bone marrow, in ECG-triggered MRA of the leg and foot.

In certain MRA studies, it is important to suppress the contribution of fat, bone marrow and other non-blood tissues. This can be done by using subtraction MRA. In subtraction MRA, a mask image to which blood makes little or no contribution is subtracted from an angiographic image to which blood makes a major contribution. The resulting subtraction image emphasizes the image contribution of the blood and thereby makes it easier for the radiologist to visualize the patient's blood vessels.

It is known to form a subtraction image of a thin slice of interest by using a mask image acquired during the diastolic phase of the patient's heart cycle (when bloodflow is slow) and an angiographic image of the slice of interest acquired during the systolic phase of the patient's heart cycle (when bloodflow is rapid). However, it is difficult to obtain a high-quality subtraction image from a subtraction MRA study of a patient's leg.

One reason for this difficulty is that in peripheral regions of the body such as the legs, regurgitated arterial bloodflow (i.e. arterial bloodflow that is reversed in direction) exists. Such regurgitated arterial bloodflow may be unsaturated, and therefore may contribute to (and consequently contaminate) the mask image of the slice of interest. It is conventional to reduce or eliminate the signal from bloodflow in the direction opposite ordinary arterial bloodflow (e.g. venous bloodflow) by creating a saturation slab on the arterially downstream side of the slice of interest. However, in instances where bloodflow is regurgitated, such measures are not sufficient. This is because it is impractical to create a sharply-defined region in space that is fully saturated, while the surrounding region is fully unsaturated. Such an idealized fully saturated region is said to have a rectangular slice or saturation profile. Likewise, it is impractical to select the slice of interest in such a way as to create a rectangular slice profile. All practical saturation slabs and slices of interest are non-rectangular, i.e. all saturation slabs have transition zones of partial saturation at their upstream and downstream ends. Thus, while the signal from regurgitated arterial blood could be eliminated by means of a rectangular saturation profile precisely mated to a rectangular slice profile so as to eliminate any gap between them, this is impractical. To avoid saturating the blood within the slice of interest, it is common to space the slice to be imaged apart from the saturation slab and to thereby form a gap. Arterial blood within this gap will be partially saturated or unsaturated, and regurgitation of such blood may cause contamination of the mask image. A contaminated mask image will, as discussed below, produce a degraded subtraction image.

Another reason why it is difficult to produce a high quality subtraction MRA image of the leg has to do with the shortness of the relevant part of the patient's cardiac cycle. It is desirable to collect as much diastolic as systolic data within each heart cycle, so that angiographic and mask images of the same resolution may be acquired rapidly. The post-regurgitation duration of diastole does not last very long. Unless the patient has a very slow heart rate, or unless the amount of data collected during systole and diastole is unreasonably reduced, the post-regurgitation duration of diastole is not long enough to acquire a mask image of the same resolution as the angiographic (systolic) image. For this reason, it is presently impractical to begin acquiring the mask image after regurgitated bloodflow has ceased.

Hence, as explained above, in a subtraction MRA study of the leg, it is difficult to make sure that the mask image has sufficient resolution and is free from contamination. And, while it might be possible to improve the quality of the mask image by acquiring the mask and angiographic image data in separate acquisitions, this is also impractical. This would double the time required for the MR study. Furthermore, the patient would be more likely to move in the meantime, and such movement between acquisition of the images would degrade the diagnostic value of the resulting subtraction image.

It would therefore be advantageous to provide method and apparatus for producing a subtraction MR angiographic image of a slice of interest in a living patient in which diagnostically adequate and equivalent amounts of systolic and diastolic MR image data could be acquired during each cardiac cycle, and in which the diastolic MR image data would be uncontaminated by regurgitated arterial blood.

One object of the invention is to provide method and apparatus for producing a subtraction MR angiographic image of a slice of interest in a living patient, which would be suitable for use in peripheral MR studies, and particularly MR studies of the foot and lower leg.

Another object of the invention is to provide such method and apparatus in which equal amounts of MR mask image data and MR angiographic image data could be acquired during each cardiac cycle.

Still a further object of the invention is, in general, to improve on known methods and apparatus of this general type.

In accordance with the invention, a saturation slab is established immediately adjacent the slice to be imaged, and slightly overlapping the slice on its arterially downstream side. This prevents the existence of any gap between the slice and the saturation slab, and therefore insures that all regurgitated blood is saturated and does not contribute to the mask image. Significantly, this saturation slab is not established before each acquisition of MR image data during the cardiac cycle; this would partially saturate the systolic blood and reduce its contribution to the angiographic image. Likewise, this saturation slab is not established repeatedly during acquisition of diastolic MR image data; this would diminish the MR signal produced from the stationary tissues and would thereby degrade the mask image. Such a degraded mask image would produce an incomplete subtraction from the angiographic image acquired during systole and would consequently fail to suppress the image contribution from the stationary tissues.

Advantageously, and in accordance with the preferred embodiment, the patient's cardiac cycle is monitored and MR image data are acquired from the slice of interest during the systole phase of a particular cardiac cycle to form an angiographic image. Further in accordance with the preferred embodiment, the above-mentioned saturation slab is temporarily established at the end of the antegrade bloodflow during systole (i.e. before the beginning of regurgitated bloodflow during diastole) and diastolic MR image data are acquired immediately after such establishment has ceased, to form a mask image. Because this saturation slab is turned off while diastolic MR image data are acquired, the tissue within the slice of interest that is partially (or completely) saturated by the saturation slab recovers much of the magnetization previously lost to saturation. This increases the brightness of the stationary tissue in the mask image, and reduces the brightness of this tissue in the subtraction image. (As is conventional, the pulse sequences used to acquire MR image data may—and advantageously do—contain conventional RF saturation pulses. These have nothing to do with the referenced saturation slab.)

To achieve the best possible subtraction image, i.e. to establish an image in which the contribution of the stationary tissues has been eliminated as completely as possible, it is advantageous to match the intensity of the stationary tissues in the angiographic image to the intensity of the stationary tissues in the mask image. To do this, the saturation slab may additionally be temporarily established at an earlier point in the cardiac cycle, namely, just prior to acquisition of systolic MR image data. In this preferred embodiment, the stationary tissues are similarly partially saturated not only during diastole, but during systole as well.

Because the saturation slab eliminates the MR signal from regurgitated arterial blood, acquisition of diastolic MR image data for the mask image can begin immediately after the saturation slab has been established. This permits the acquisition of MR image data to take place over a sufficiently long time that the resolution of mask image can be equivalent to the resolution of the angiographic image.

BRIEF DESCRIPTION OF THE DRAWINGS

The invention will be better understood with reference to the accompanying exemplary and non-limiting drawings, in which.

DETAILED DESCRIPTION OF PREFERRED EMBODIMENTS

The drawings below have been simplified and are not to scale. In all Figures, the same element is always indicated using the same reference number.

Figure 1:
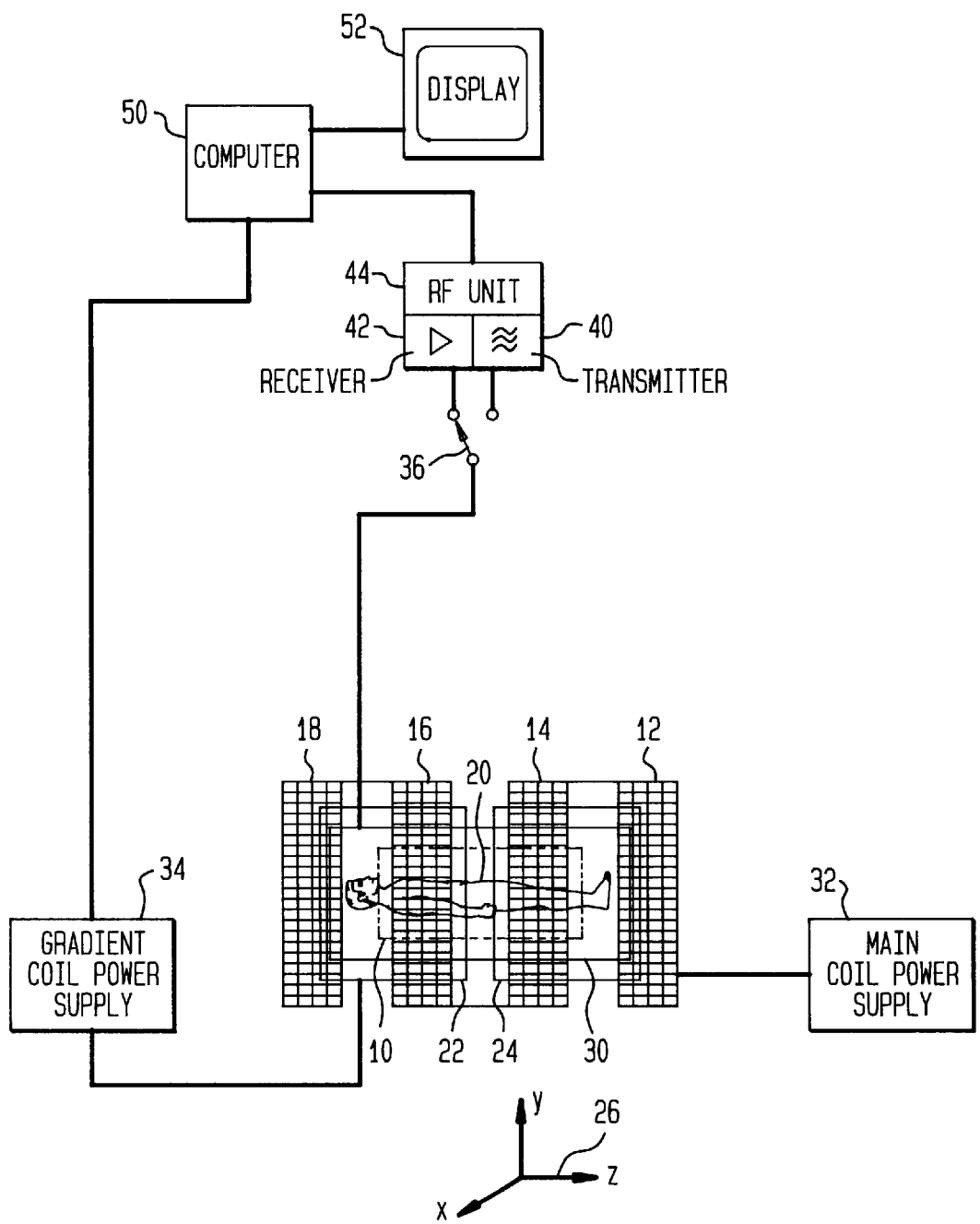
FIG. 1 schematically illustrates conventional MR apparatus.

A conventional MR system such as that shown in FIG. 1 has main field coils 12, 14, 16 and 18, which are used to establish the main field in which the patient 20 is placed. Gradient coils 22 and 24, together with other like coils on the other side of the patient, establish a gradient magnetic field along the X direction of the coordinate system 26 of the MR system. Other gradient coils (not shown) establish a gradient magnetic field along the Y and Z directions. An RF coil 30 is used for transmit and receive functions. The radio frequency (RF) coil 30 delivers RF signals to the patient 20 within the examination region 10 and thereby induces resonance of e.g. hydrogen nuclei in the patient 20 which are within the slice of interest. This causes the production of magnetic resonance signals from such hydrogen nuclei; the magnetic resonance signals are picked up by the RF coil 30 and computer-processed to form an image of the slice of interest.

The main field coils 12, 14, 16 and 18 are energized by a main coil power supply 32, and the gradient coils (including the coils 22 and 24 but not limited to them) are energized by a gradient coil power supply 34. The gradient coil power supply 34 is in turn controlled by a computer 50.

In use, the computer 50 causes RF pulses to be produced by the RF unit 44. The pulses are then routed through a transmitter 40 and a switch 36 to the RF coil 30. This induces the MR effect in e.g. hydrogen nuclei within the patient 20. Then, the switch 36 is thrown to its other position, MR resonance signals from the patient 20 are picked up by the RF coil 30, received via the receiver 42 and routed to the computer 50 via the RF unit 44. The computer 50 is then used to reconstruct MR images of the slice of interest, and these reconstructed MR images can be output to a display 52 or other output device.

In conventional MR angiography, the MR signal from a sample in a region of space may be substantially reduced by "saturating" that region. Before such saturation, the nuclear spins in the sample within the region have a net magnetization along the Z direction. To saturate the sample within the region, an RF pre-pulse and one or more gradient pulses are applied to the RF and gradient coils respectively. This nutates, or flips, the spins of the nuclei within the desired slab of the sample towards the X-Y plane, thereby eliminating the net magnetization along the Z direction, orienting the nuclear spins variously within the X-Y plane ("dephasing" the nuclear spins) and consequently preventing the nuclei with nutated spins from producing an MR signal. In this state, the nuclei are "saturated", and the region in which this saturation exists is known as the "saturation slab".

Although the saturated nuclei gradually regain the ability to produce an MR signal as natural relaxation processes cause the nuclei to regain a net magnetization along the Z direction, this process is a function of time alone and it occurs relatively slowly for hydrogen nuclei in the blood. As a result, the saturated nuclei produce a reduced MR signal until long after the interval in which MR signals from the predetermined desired slice are picked up by the RF coil 30, routed to the computer 50, and used to construct MR images.

It may thus be understood that nuclei within the saturation slab during the RF pre-pulse and gradient pulse(s) do not produce an MR signal during the window of time when the MR system "looks" for such a signal. As a result, as long as the nuclei remain saturated, they will not contribute to an MR image, even if they are physically moved (as is the case with hydrogen nuclei in the blood, which nuclei move as the blood flows through the circulatory system).

For purposes of illustration, an impractical cardiac-triggered (in this instance, R-wave triggered) subtraction MRA study of the leg will now be described in connection with FIG. 2.

Figure 2:
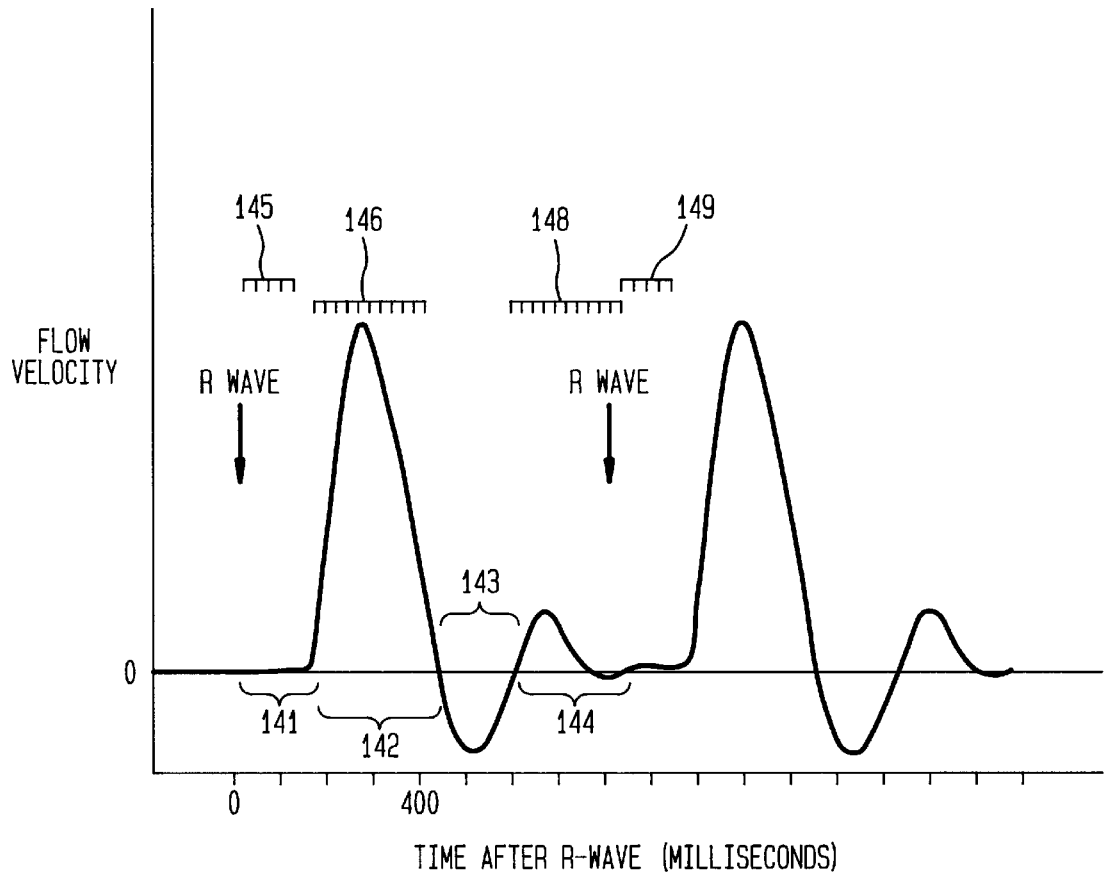
FIG. 2 schematically illustrates the interplay between a patient's cardiac cycle and arterial bloodflow, and data acquisition in a hypothetical cardiac-triggered, subtraction MRA study of the patient's lower leg.

In FIG. 2, arterial bloodflow velocity in the leg is plotted along the Y axis and time is plotted along the X axis. As is shown there, during time period 141, the blood pressure wave created by systolic contraction of the heart makes its way to the slice of interest in the patient's leg; arterial bloodflow velocity rises above 0 approximately 150 msec after the patient's R-wave (which, because it is used as the trigger, is considered to begin a particular cardiac cycle). During time period 142, antegrade arterial bloodflow velocity then increases to a maximum value and subsequently decreases to 0 about 400 msec after the patient's R-wave. Subsequently, during time period 143, arterial bloodflow begins to be regurgitated. This continues for approximately 150 msec. Thereafter, the cardiac cycle continues for the duration of time period 144, until a new R-wave is detected. For convenience, the time period 142 is said to occur during "systole" even though it takes a certain period of time for the pumping action of the heart to have an effect in the patient's leg;, the time periods 143 and 144 are similarly said to occur during "diastole". Although the durations of the time periods 141, 142, 143 and 144 change with the patient's heart rate, the time period 144 changes more than the others.

During the time period 141, an RF pre-pulse sequence 145 is typically applied to the slice of interest to bring the magnetization into a steady state. During time period 142, MR angiographic image data are acquired from the slice of interest. In the example illustrated, this is done by acquiring 11 lines of data during each heart cycle using an ECG-triggered, 2-D gradient echo sequence 146 in which the echo time is 6.2 msec, bandwidth is 195 Hz/pixel, and the effective repetition time is 21 msec.

Let it be assumed that MR image data for the mask image are to be acquired during time period 144, using a pulse sequence 148. (For purposes of illustration, the pulse sequence 148 is assumed to be identical to the pulse sequence 146.) Under these circumstances, there is a risk that the pulse sequence 148 will not be finished before the next R-wave is generated by the patient's heart. (This is because, as stated above, the time period 144 varies with the patient's heart rate. If the patient's heart rate is elevated, the time period 144 can be substantially shorter than shown in FIG. 2.) If the pulse sequence 148 is not finished by the time the next R-wave is generated, it will overlap and interfere with the RF pulse sequence 149 (the counterpart of the previous pulse sequence 145 in the previous cardiac cycle). Although it would be possible to shorten the pulse sequence 148 so that it would surely be finished by the time the next R-wave was generated, this would also be unsatisfactory because this would reduce the quantity of MR mask image data acquired and the mask image a) would then have inferior resolution compared to the angiographic image, or b) would require additional cardiac cycles to obtain the desired resolution. For these reasons, it is not practical to wait for regurgitated arterial bloodflow to cease before beginning acquisition of MR mask image data from the slice of interest.

Furthermore, if MR mask image data were alternatively to be acquired during regurgitation in time period 143 using conventional techniques, the mask image would be contaminated. The reason for this will now be explained with reference to FIGS. 3A, 3B, and 3C.

Figure 3A:
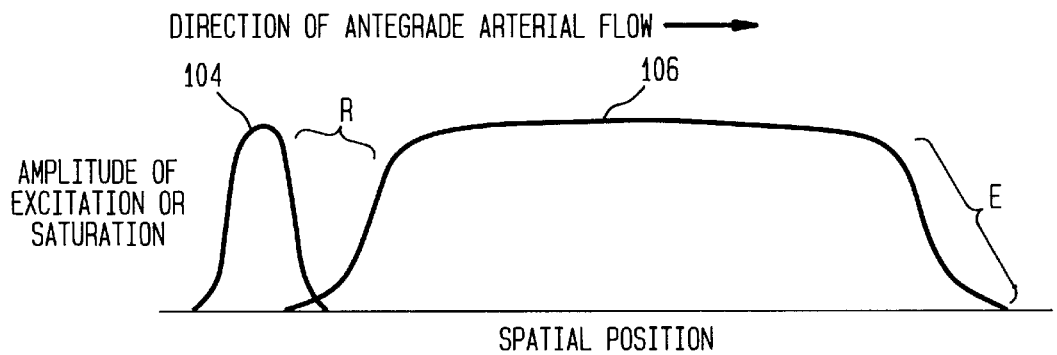
FIG. 3A schematically illustrates how a conventional saturation slab is used to saturate venous bloodflow.

As shown in FIG. 3A, a conventional saturation slab 106 (such as is used to saturate venous bloodflow in MRA studies) produces a gap at region R between the saturation slab 106 and the slice of interest 104. This is because it is impractical to produce a saturation slab 106 (and likewise an excitation slice of interest 104) that has a perfectly rectangular profile. The ends E of the profile of every saturation slab 106 always have a significant spatial extent. As a result, the saturation slab 106 produces only partial saturation in the region R.

Figure 3B:
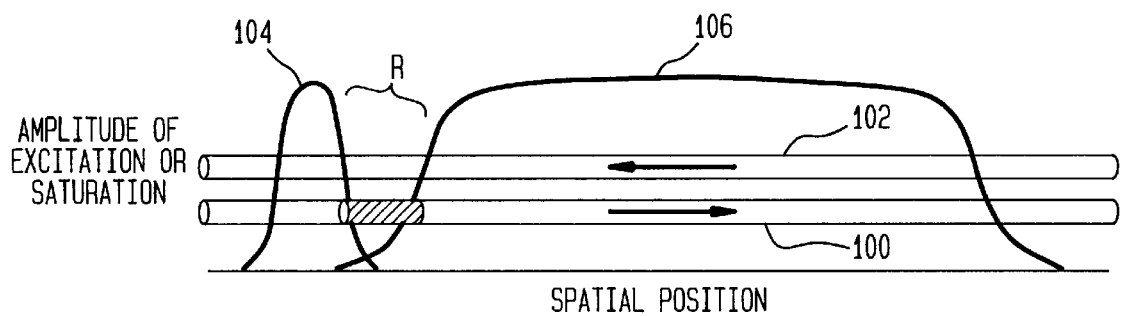
FIGS. 3B and 3C schematically illustrate how regurgitated arterial blood can contaminate a mask image during a conventional subtraction MRA study.
Figure 3C:
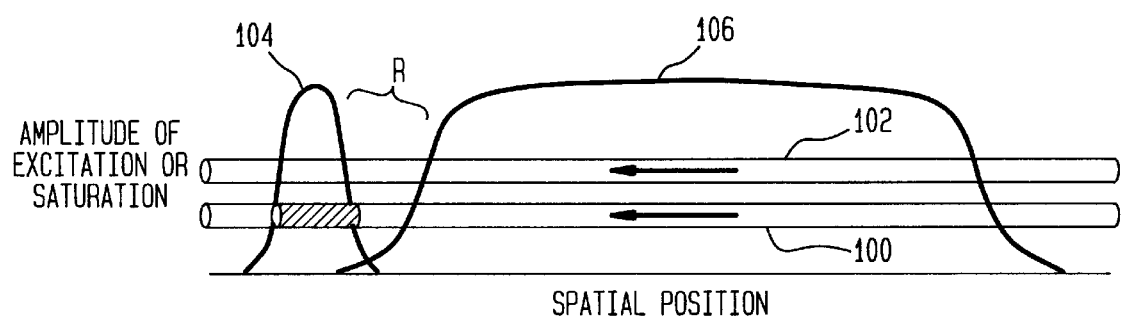

FIG. 3B shows an artery 100, a vein 102, a slice of interest 104, and the saturation slab 106, as used in a conventional MRA study to suppress the image contribution of venous bloodflow. During systole, bloodflow occurs in the directions shown. Because the saturation slab 106 is spaced downstream from the slice of interest 104 in the direction of arterial bloodflow, the blood in the region R of the artery 100 (region R is located between the slice of interest 104 and the saturation slab 106) is unsaturated and therefore capable of producing an MR signal. Hence, when regurgitation occurs, as is illustrated in FIG. 3C, the blood from region R flows into the slice of interest 104, where it contributes to the mask image and therefore contaminates it. This contamination is disadvantageous because the purpose of a subtraction image is to suppress the background (e.g. fat, bone marrow) while maintaining an intense MR signal from the blood. If the mask image is contaminated by the image contribution of moving blood, the resulting subtraction image of the blood will have a reduced intensity.

Figure 4:
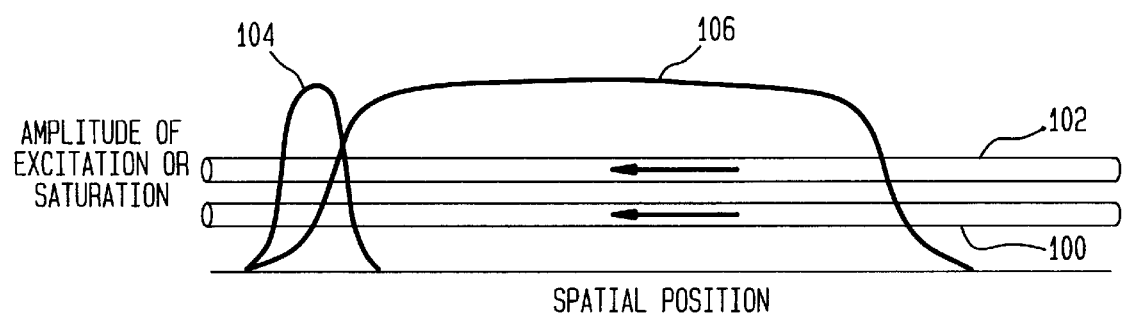
FIG. 4 schematically illustrates the positioning of a saturation slab in accordance with a preferred embodiment of the invention.

In accordance with the preferred embodiment of the invention, the saturation slab 106 is placed immediately adjacent to, and slightly overlapping, the arterially downstream side of the slice of interest 104, temporally at or near the beginning of regurgitation (see FIG. 4). This saturates the to-be-regurgitated blood, preventing it from producing an MR signal when it is regurgitated into the slice of interest 104 and therefore preventing it from contaminating the mask image of the slice of interest 104. Then, acquisition of diastolic MR image data commences shortly afterward.

Figure 5:
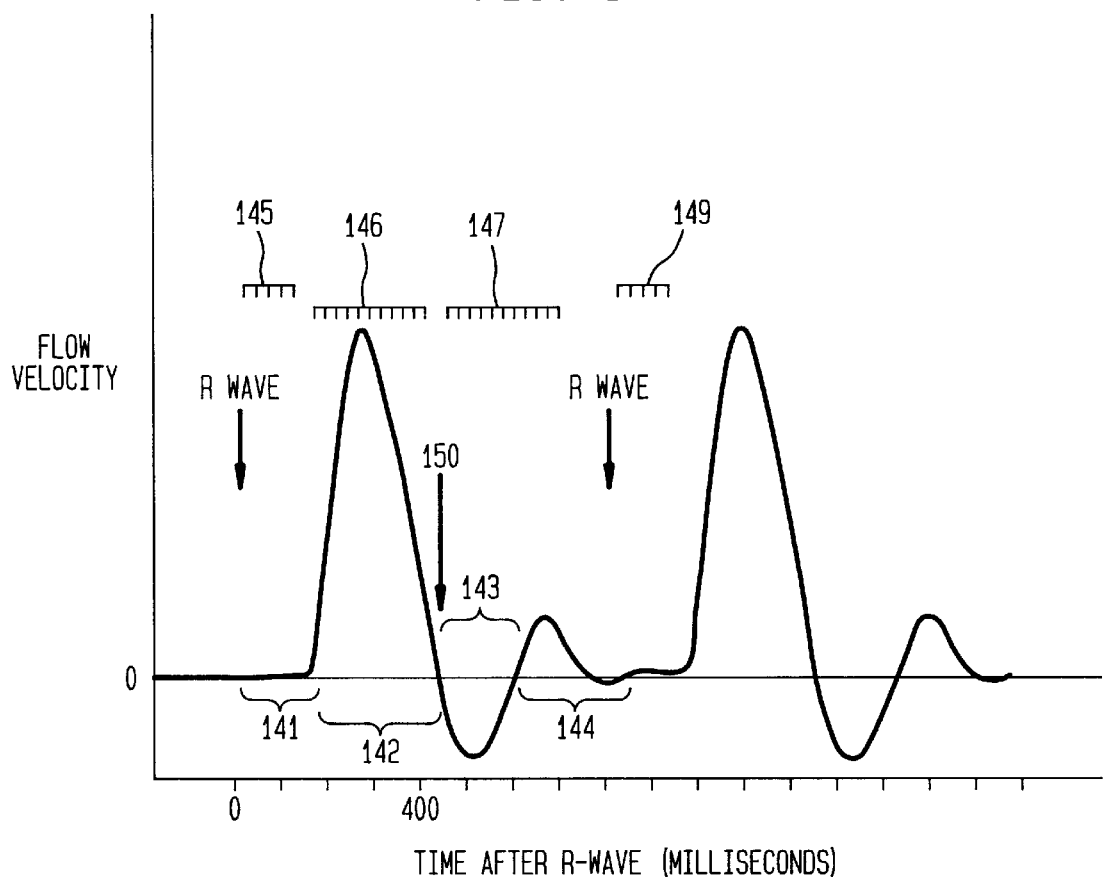
FIG. 5 schematically illustrates the interplay between a patient's cardiac cycle and arterial bloodflow, and data acquisition in a cardiac-triggered, subtraction MRA study of the patient's leg in accordance with a preferred embodiment of the invention.
Figure 6:
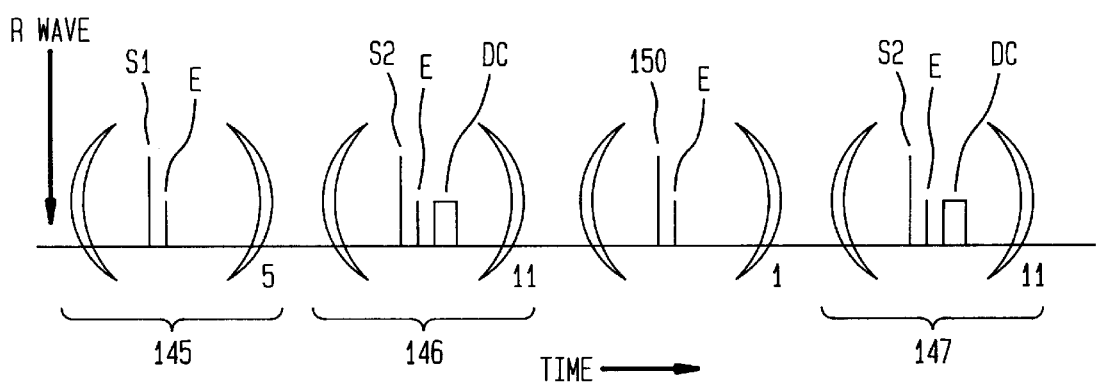
FIG. 6 schematically illustrates pulse sequences used in the preferred embodiment of the invention.

In accordance with the preferred embodiment as illustrated in FIG. 5, the RF pre-pulse sequence 145 is applied to the slice of interest during the time period 141, as described above. (The sequence 145 is shown in more detail in FIG. 6, which is described below.) Likewise as described above, acquisition of systolic MR image data from the slice of interest 104 begins approximately 150 msec after the patient's R-wave is detected, and takes place during the time period 142. (Systolic MR image data acquisition is advantageously timed to begin as arterial bloodflow velocity begins to rise above 0.) An MR pulse sequence 146 suitable for this data acquisition is illustrated in FIG. 6, and is described below. This sequence is an ECG-triggered, 2-D gradient echo sequence with gradient motion nulling, and in the preferred embodiment, 11 lines of data are acquired for both the systolic and diastolic images during each heart cycle. A suitable echo time is 6.2 msec, a suitable bandwidth is 195 Hz/pixel, and a suitable effective repetition time is 21 msec. Such an image acquisition, which takes place during time interval 146, lasts approximately 231 msec.

Shortly after the end of this MR image data acquisition, and just before the onset of regurgitated arterial bloodflow, a saturation pulse 150 is delivered at the beginning of the time interval 143. This establishes—for a predetermined time—a saturation slab 106 immediately adjacent the slice of interest 104 and overlapping its arterially downstream side. As a result, any arterial blood regurgitated into the slice of interest 104 is saturated, and does not contribute to the mask image of the slice of interest 104.

After the saturation slab 106 has been eliminated, and while arterial bloodflow is being regurgitated into the slice of interest 104, diastolic MR image data are acquired during the time intervals 143 and 144. (The saturation slab 106 remains only long enough to saturate the to-be-regurgitated blood.) This data acquisition is carried out using pulse sequence 147 (which in the preferred embodiment is similar to the pulse sequence 146 but lacks gradient motion nulling in order that the blood signal be further reduced). The pulse sequence 147 is likewise illustrated in FIG. 6 and described in more detail below). (This similarity between the pulse sequences 146 and 147 is advantageous, but not required. It is convenient if the pulse sequences are similar, but the pulse sequences may alternatively be dissimilar to each other. Also, while it is advantageous for the two image acquisitions to be of identical durations, this is only for convenience. One image acquisition may be longer than the other one.)

In accordance with the preferred embodiment of the invention, wherein diastolic MR image data for the mask image is acquired during the time periods 143 and 144, the time available for such data collection is increased by approximately 150 msec without contaminating the mask image. This is especially useful for patients with rapid heart rates.

Once both data acquisitions have been carried out, a mask image formed from the diastolic MR image data can be subtracted from an angiographic image formed from the systolic MR image data. The resulting subtraction image suppresses the background from e.g. fat and bone marrow.

While the MR data acquisitions in the preferred embodiment last approximately 231 msec, this is only preferred; the invention does not reside in the duration of MR data acquisition. Likewise, while systolic data acquisition begins approximately 150 msec after the detection of the patient's R-wave, this is likewise only preferred and this time interval can be varied. Also, while in the preferred embodiment portions of the angiographic and mask images are acquired during the same cardiac cycle, this is only preferred. If the patient is immobilized, it may be possible to acquire these images separately.

While in accordance with the preferred embodiment the pulse 150 is applied immediately before regurgitated arterial bloodflow, this is only preferred. This pulse 150 can alternatively be applied earlier or later. It must not be applied so early that the blood that it saturates will fail to be regurgitated into the slice of interest 104. It must not be applied so late as to make the time available for diastolic MR image data acquisition insufficient.

The overlap between the saturation slab 106 and the slice of interest 104 must be adequate to make sure that regurgitated blood does not make a significant contribution to the mask image. The overlap between the saturation slab 106 and the slice of interest 104 insures that most (or all) regurgitated blood is saturated and that no unsaturated (i.e. MR signal-producing) regurgitated blood makes its way into the mask image. (If only a tiny volume of such unsaturated blood is so imaged, this is of little importance and does not interfere with the usefulness of the final MRA subtraction image.)

As shown in FIG. 6, the pulse sequence 145 contains five repetitions of a two-pulse subsequence. Saturation pulses S1 may be of the conventional type or of the overlapping type mentioned above. The number and type of these pulses may be adjusted to obtain the optimal balance of brightness of stationary tissue and blood. This subsequence also advantageously includes an RF excitation pulse E. The pulse sequence 146 contains eleven repetitions of another subsequence. This other subsequence contains a conventional RF saturation pulse S2, an excitation pulse E, and a data collection interval DC (during which the induced MR signal is received). While it is possible to use a single saturation pulse 150 in accordance with the invention, it is advantageous to follow it with an excitation pulse E, and this is preferred. The pulse sequence 147 is identical to the pulse sequence 146. Persons skilled in the art know that the above-described RF pulses may themselves be superpositions of other RF pulses; this is not a part of the invention and will not be discussed further.

Figure 7:
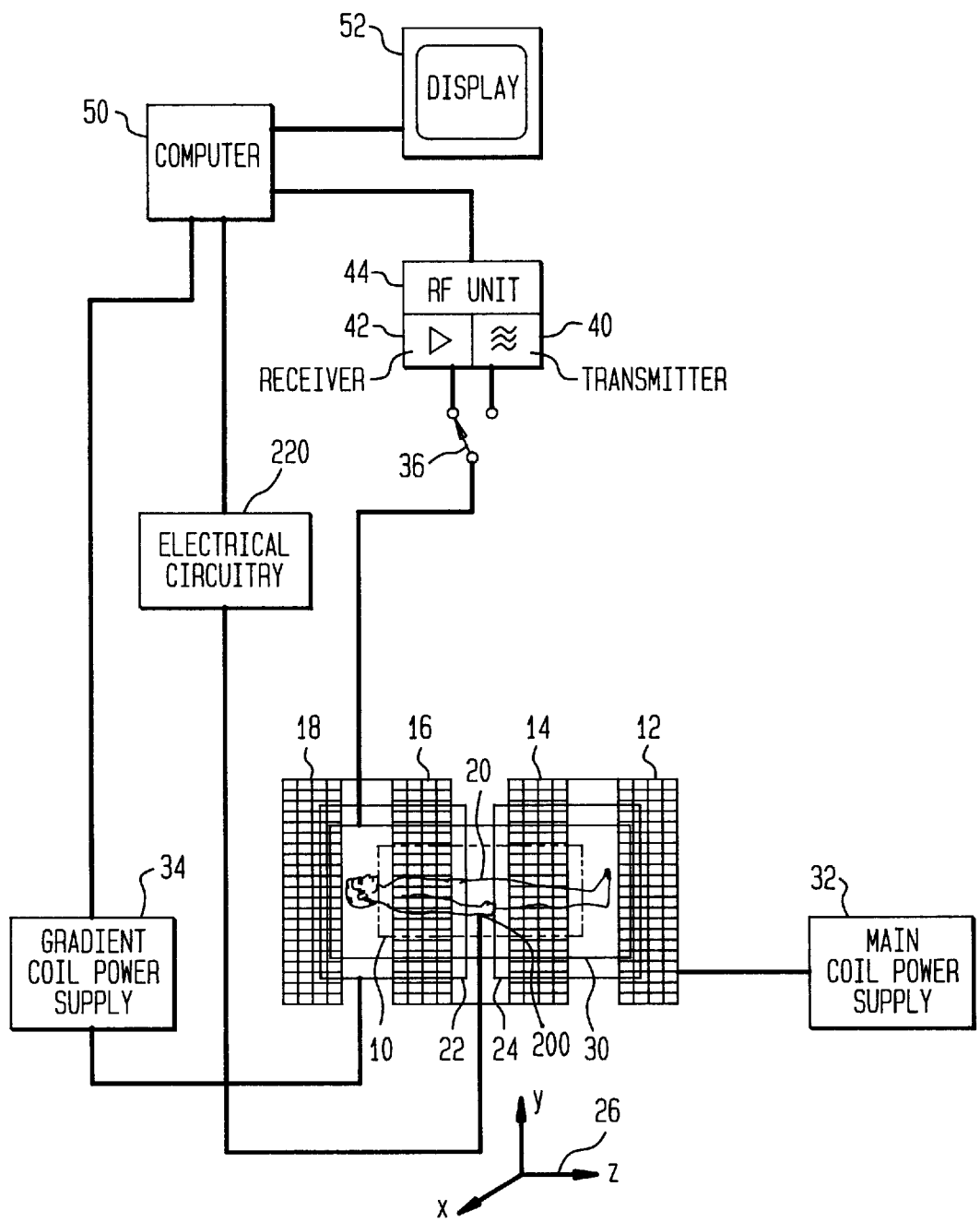
FIG. 7 schematically illustrates MR apparatus in accordance with a preferred embodiment of the invention.

To carry out the preferred embodiment of the invention, cardiac electrodes 200 (see FIG. 7) may be connected to the patient. Electrical circuitry 220 may be used to analyze the patient's cardiac cycle and to output trigger signals to the computer 50 at appropriate times during the cardiac cycle.

While one or more preferred embodiments have been described above, the scope of the invention is limited only by the following claims:

What is claimed is:

1. A method for producing a subtraction MR angiographic image of a slice of interest in a living patient, comprising the following steps:

monitoring the patient's cardiac cycle to detect the beginning thereof;

acquiring MR image data from the slice during systole;

establishing a saturation slab immediately adjacent the slice and slightly overlapping it on its arterially downstream side, said establishing step being carried out at or near the beginning of blood regurgitation; and acquiring MR image data from the slice during diastole.

2. The method of claim 1, further comprising the step of forming a subtraction image from systolic MR data and diastolic MR data.

3. The method of claim 2, wherein the systolic MR data are used to form an angiographic image and the diastolic MR data are used to form a mask image.

4. The method of claim 1, wherein during each cardiac cycle, both of said acquiring steps, and said establishing step, are carried out.

5. A method for producing a fat-suppressed MR angiographic image of a slice of interest in a leg of a living patient, comprising the following steps:

monitoring the patient's cardiac cycle to detect the beginning thereof;

acquiring MR image data from the slice during systole;

establishing a saturation slab immediately adjacent to the slice and slightly overlapping it on its arterially downstream side, said establishing step being carried out during the same cardiac cycle and at or near the beginning of blood regurgitation;

acquiring MR image data from the slice during diastole; and forming a subtraction image from the systolic MR image data and the diastolic MR image data.

6. Apparatus for producing an MR angiographic image with suppressed stationary tissue of a slice of interest in a living patient, comprising:

means for monitoring the patient's cardiac cycle to detect the beginning thereof;

means for acquiring MR image data from the slice during systole;

means for establishing a saturation slab immediately adjacent to the slice and slightly overlapping it on its arterially downstream side, said saturation slab being established out at or near the beginning of blood regurgitation; and means for acquiring MR image data from the slice during diastole.

* * * * *